(12) United States Patent
Smith et al.

(10) Patent No.: US 6,657,106 B2
(45) Date of Patent: Dec. 2, 2003

(54) REMOVAL OF METALS FROM CONTAMINATED SUBSTRATES BY PLANTS

(75) Inventors: James Andrew Charles Smith, Islip (GB); Ute Krämer, Bielefeld (DE); Alan John Martin Baker, Sheffield (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/029,941

(22) PCT Filed: Sep. 12, 1996

(86) PCT No.: PCT/GB96/02264

§ 371 (c)(1),
(2), (4) Date: Apr. 16, 1998

(87) PCT Pub. No.: WO97/10346

PCT Pub. Date: Mar. 20, 1997

(65) Prior Publication Data

US 2002/0157128 A1 Oct. 24, 2002

(30) Foreign Application Priority Data

Sep. 12, 1995 (GB) ............................................. 9518599

(51) Int. Cl.$^7$ ........................ C12N 15/09; C12N 15/31; C12N 15/82; A01H 5/00
(52) U.S. Cl. ...................... 800/278; 800/298; 800/295; 800/288; 800/306; 435/69.1; 435/320.1; 435/419; 435/468; 536/23.1; 536/24.1; 536/23.7
(58) Field of Search ................................. 800/278, 298, 800/295, 306, 288; 435/69.1, 320.1, 419, 468; 536/23.2, 24.1, 23.7

(56) References Cited

FOREIGN PATENT DOCUMENTS

WO        94/29466        12/1994

OTHER PUBLICATIONS

Pan et al. Plant Molecular Biology. 1994. vol. 24: 341–351, 1994.*
Napoli et al. The Plant Cell. 1989. vol. 2: 278–289, 1989.*
Jovanovic et al. Nucleic Acid Research. 1990. vol. 18: 3634, 1990.*
Valvekens et al. The Proc. Natl. Acad. Sci. 1988. vol. 85: 5536–5540, 1988.*

M.P. Bernal et al., "Comparison of the chemical changes in the rhizosphere of the nickel hyperaccumulator *Alyssum murale* with the non–accumulator *Raphanus sativus*", Plant and Soil, 164: pp. 251–259, 1994.

A.J.M. Baker et al., "The possibility of in situ heavy metal decontamination of polluted soils using crops of metal–accumulating plants", Resources, Conservation and Recycling, vol. 11, pp. 41–49, Jun. 30, 1994.

U. Kramer et al., "Free histidine as a metal chelator in plants that accumulate nickel", Letters to Nature, vol. 379, pp. 635–638, Feb. 15, 1996.

\* cited by examiner

*Primary Examiner*—Elizabeth F. McElwain
*Assistant Examiner*—Medina A. Ibrahim
(74) *Attorney, Agent, or Firm*—Wenderoth, Lind & Ponack, L.L.P.

(57) ABSTRACT

A method of removing metal from a metal-containing substrate is provided. The method comprises (1) providing modified plants having an improved metal accumulating capability compared to unmodified plants by virtue of an increase in the concentration of histidine within the modified plants and (2) maintaining at least one such modified plant on the metal containing substrate under conditions such that the modified plant accumulates the metal from the substrate. The modified plant can be genetically engineered so as to be capable of increased production of histidine. Further, the increase in histidine concentration within the modified plants can also be achieved by administering a formulation comprising an effective concentration of histidine to the plants. A recombinant vector capable of transforming selected plant cells to augment the concentration of histidine in the plant cell, and a plant cell, plant cell culture or transgenic plant transformed with such a vector is also disclosed.

8 Claims, 4 Drawing Sheets

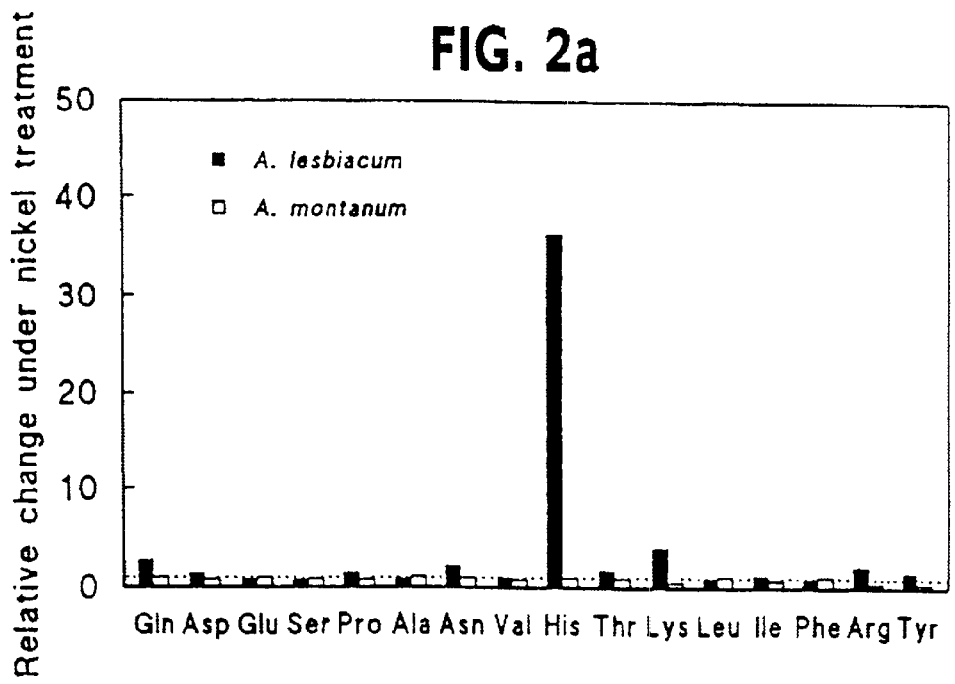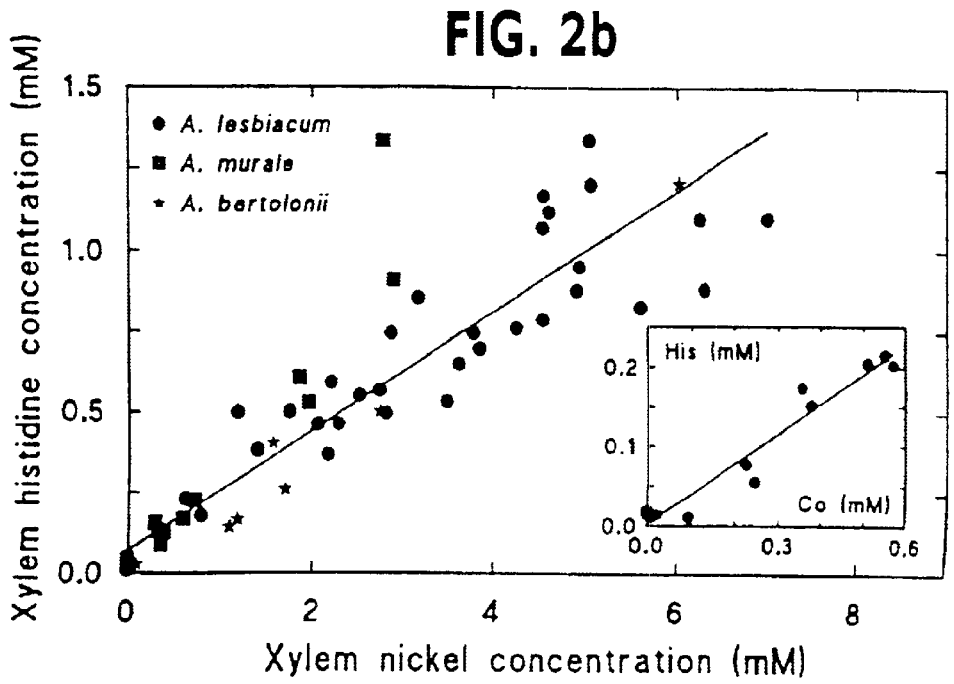

SEQUENCE LISTING

<160> NUMBER OF SEQ ID NOS: 6

<210> SEQ ID NO 1
<211> LENGTH: 36
<212> TYPE: DNA
<213> ORGANISM: Unknown
<220> FEATURE:
<223> OTHER INFORMATION: Description of Unknown Organism:SYNTHETIC DNA
      PRIMER

<400> SEQUENCE: 1
acgcgcatgc atgagtcaga agtatctttt tatcga                              36

<210> SEQ ID NO 2
<211> LENGTH: 32
<212> TYPE: DNA
<213> ORGANISM: Unknown
<220> FEATURE:
<223> OTHER INFORMATION: Description of Unknown Organism:SYNTHETIC DNA
      PRIMER

<400> SEQUENCE: 2
acgcgtcgac ttacagcacc ctttcgacga gg                                  32

<210> SEQ ID NO 3
<211> LENGTH: 36
<212> TYPE: DNA
<213> ORGANISM: Unknown
<220> FEATURE:
<223> OTHER INFORMATION: Description of Unknown Organism:SYNTHETIC DNA
      PRIMER

<400> SEQUENCE: 3
acgcgcatgc atgagcttta acacaatcat tgactg                              36

<210> SEQ ID NO 4
<211> LENGTH: 32
<212> TYPE: DNA
<213> ORGANISM: Unknown
<220> FEATURE:
<223> OTHER INFORMATION: Description of Unknown Organism:SYNTHETIC DNA
      PRIMER

<400> SEQUENCE: 4
acgcgtcgac tcatgcttgc tccttaaggg cg                                  32

<210> SEQ ID NO 5
<211> LENGTH: 34
<212> TYPE: DNA
<213> ORGANISM: Unknown
<220> FEATURE:
<223> OTHER INFORMATION: Description of Unknown Organism:SYNTHETIC DNA
      PRIMER

<400> SEQUENCE: 5
acgcgcatgc atgacagaca acactcgttt acgc                                34

<210> SEQ ID NO 6
<211> LENGTH: 34
<212> TYPE: DNA

```
-continued

<213> ORGANISM: Unknown
<220> FEATURE:
<223> OTHER INFORMATION: Description of Unknown Organism:SYNTHETIC DNA
      PRIMER

<400> SEQUENCE: 6
acgcgtcgac tcactccatc atcttctcaa tcgg                              34
```

REMOVAL OF METALS FROM CONTAMINATED SUBSTRATES BY PLANTS

This application is a U.S. national stage of International Application No. PCT/GB96/02264 filed Sep. 12, 1996.

BACKGROUND OF THE INVENTION

1. Field of the Invention

This invention is concerned with the phenomenon of hyperaccumulation of metals in plants and the removal of metals from contaminated substrates by plants. The invention relates in particular to methods for removing metals from soil or other environments using modified plants having an increased capacity for metal uptake, and to methods for obtaining such plants. The invention is also concerned with transgenic plants having an increased capacity for metal uptake, and to recombinant vectors and transformed plant cells used to obtain the transgenic plants.

2. Description of the Related Art

Many soils are contaminated by metals that derive from sources such as mine workings, metal-processing industries, atmospheric depositions, the power and fuel industries, deposition of contaminated sewage sludge, and others. These contaminated substrates pose serious human health problems, are deleterious to the environment, and can render crop cultivation either inadvisable (because of the health hazard from the plant products) or impractical (because of the toxicity of the metals towards plants). These problems are becoming more acute in many regions, for example as a result of increased deposition of contaminated sewage sludge on land rather than at sea.

Conventional approaches for decontaminating metal-polluted soils have relied on physical methods such as landfilling (the excavation and removal of soil to a landfill site designated for hazardous waste), fixation or immobilization (such as infiltration with cement or by vitrification), or leaching (for example with strong acids to desorb the metal ions) (see Salt, D. E. et al. (1995) Bio/Technology 13, 468–474). These methods are not only expensive but are environmentally less than ideal, for example because they tend to destroy soil structure (as well as the microbial organisms in the soil), and can give rise to secondary pollution in run-off water. Thus it has been recognized that removal of metals from contaminated soils by metal-tolerant plants might provide an alternative and cost-effective technology for environmental clean-up, a concept known as "phytoremediation" (Chaney, R. L. (1983) In Land Treatment of Hazardous Wastes, eds Parr, J. F., Marsh, P. B. and Kla, J. M., pp 50–76. Noyes Data Corp., Park Ridge, N.J.; Salt et al. (1995), loc. cit.).

To date, the application of plants in phytoremediation has been limited by the severe toxicity of most metal ions to the majority of plant species. However, a number of plant species are known that are both relatively metal tolerant and capable of accumulating metals to high concentrations in their above-ground biomass. These plants are known as "metal hyperaccumulators", of which several hundred species have so far been described (Baker, A. J. M. and Brooks, R. R. (1989) Biorecovery 1, 81–126). These plants have favourable characteristics for bioremediation, since the above-ground parts (leaves and stems) can be readily harvested, and the metal-rich residues processed in a controlled manner. Successive cycles of crops of these metal-hyperaccumulator plants would be expected to lead to progressive decontamination of the soils, and this has been demonstrated (Baker, A. J. M. et al. (1994) Resources, Conservation and Recycling 11, 41–49; Brown, S. L. et al. (1994) J. Environ. Qual. 23, 1151–1157; Brown S. L. et al. (1995) Soil Sci. Soc. Am. J. 59, 125–133). However, most hyperaccumulator plants are of relatively small stature and are slow-growing, so long periods of time would be needed to decontaminate most metal-polluted substrates to acceptable levels (Baker, A. J. M. et al. (1994) loc. cit.). The definition of "metal hyperaccumulator" varies according to the metal concerned, e.g. for zinc it is >1% by dry weight, while for nickel and cobalt it is >0.1% by dry weight (see Baker, A. J. M. et al. (1994) loc. cit.).

The underlying mechanism of metal-hyperaccumulation in plants has not up to now been understood. Most theories of metal tolerance in plants have assumed that metal ions within the plant are detoxified by chelation with an appropriate high-affinity ligand (Ernst, W. H. O. et al. (1992) Acta Bot. Neerl. 41, 229–248). The most frequently suggested ligands of this type have been cysteine-rich proteins called metallothioneins (Robinson, N. J. et al. (1993) Biochem. J. 295, 1–10), including the lower-molecular-weight phytochelatins (Rauser, W. E. (1990) Annu. Rev. Biochem. 59, 61–86), and organic-acid anions such as malate, citrate and malonate (Reeves, R. D. (1992) In The Vegetation of Ultramafic (Serpentine) Soils, eds Baker, A. J. M., Proctor, J. and Reeves, R. D., pp 253–277. Intercept Press, Andover). However, the concentrations of these potential metal-chelating ligands do not respond in the proportional and metal-specific manner that would be anticipated if they had a fundamental role in the phenomenon of metal hyperaccumulation (Ernst, W. H. O. et al. (1992) loc. cit.; Reeves, R. D. (1992) loc. cit.; de Knecht, J. A. et al.(1994) Plant Physiol. 104, 255–261).

In principle, if the biochemical mechanisms responsible for metal tolerance and metal accumulation in plants were understood, this would permit the development of novel strategies for the application of plants in the clean-up of contaminated soils. For example, genetically modified plants with altered biochemical characteristics can be generated using recombinant DNA techniques ("genetic engineering"). Several reports have been published of plants genetically transformed to express one or other animal metallothionein gene, but these have given variable results. In some (but not all) experiments, an increase in tolerance towards cadmium was observed in plants expressing an animal metallothionein gene, but this appeared to be associated with a decreased cadmium accumulation in the above-ground parts of the plant (Elmayan, T. and Tepfer, M. (1994) Plant J. 6, 433–440, and references therein). Plants genetically modified in this manner thus do not appear to be suitable for the purpose of phytoremediation of contaminated soils.

Novel strategies for the application of plants in the extraction of metals from soils would be possible if the biochemical processes responsible for the phenomenon of metal hyperaccumulation were understood. The so-called "metal hyperaccumulator plants" have the ability to extract metals effectively from the soil (cf. Bernal, M. P. et al. (1994) Plant Soil 164, 251–259), to accumulate high amounts of metals in their above-ground biomass, and to tolerate metal concentrations in the soil that would be toxic to the great majority of plant species (Baker, A. J. M. and Brooks, R. R. (1989) loc. cit.). These properties are all highly desirable in plants to be used for purposes of phytoremediation. Up to now, however, there has been no clear understanding of the cellular factors responsible for these distinctive features of metal hyperaccumulator plants.

Recently, it has been observed that the amino acid histidine increases in the xylem sap of the hyperaccumulator plant *Alyssum lesbiacum* when these plants are exposed to nickel in the root medium (Kramer, U., Baker, A. J. M. and Smith, J. A. C. (1994) Abstracts of the Fifth International Symposium on the Genetics and Molecular Biology of Plant Nutrition, University of California, U.S.A., July 17–24; Smith, J. A. C., Kramer, U. and Baker, A. J. M. (1995) Meeting on Phytoremediation by Hyperaccumulator Plants—Current Research and Future Requirements, Rothamsted, UK, January 25–28; Smith, J. A. C., Kramer, U., Tibbetts, R. A. and Baker, A. J. M. (1995) Second International Conference on Serpentive Ecology, Nouméa, New Caledonia, July 31–August 5). When supplied to the xylem of excised shoots of the non-metal-accumulating species *A. montanum,* histidine apparently reduced the toxicity of nickel; also, when apparently supplied to the root medium of excised roots of this species, histidine again apparently reduced the toxicity of nickel, as manifested by an increased exudation of sap from the cut xylem and increased flux of nickel through the root system (Smith, J. A. C., Krämer, U. and Baker, A. J. M. (1995) Fourteenth Annual Symposium, Current Topics in Plant Biochemistry, Physiology and Molecular Biology, University of Missouri, Columbia, Mo.,

SUMMARY OF THE INVENTION

The present invention aims to overcome the problems associated with conventional soil decontamination methods, and to provide methods and means for decontamination of metal-polluted soils and other plant-supporting environments using phytoremediation technology.

The inventors have now discovered that the production of histidine in response to metal exposure is functionally responsible for both the high degree of metal tolerance shown by so-called "metal-hyperaccumulator plants" in the genus Alyssum and their characteristic ability to accumulate very high concentrations of metals in their shoots. We report here that the nickel accumulated within the plant is chelated with histidine. We have also demonstrated that surprisingly, by simple application of histidine as a foliar spray, the nickel tolerance of a normally non-nickel-tolerant species of Alyssum is greatly increased. We have also recognised that, given the association of the hyperaccumulation trait with a specific metabolic pathway, the transfer of a particular gene involved in that metabolic pathway to a target plant species can be used to give transgenic plants which both accumulate high concentrations of metals and show favourable growth characteristics for phytoremediation.

The present invention therefore provides in one aspect a method of removing an amount of metal from a metal-containing substrate, which method comprises:

a) identifying a metal-containing substrate;

b) providing modified plants having an improved metal accumulating capability compared to the unmodified plants by virtue of an increase in the concentration of histidine within the modified plants; and c) maintaining at least one modified plant on the metal-containing substrate under conditions such that the modified plant accumulates the metal from the substrate.

The metal-containing substrate may be a soil environment or other environment capable of supporting plant growth, and could be a purely aqueous environment.

In a preferred embodiment of the method according to the invention, the modified plants are genetically engineered plants modified so as to be capable of increased production of histidine compared to their non-modified counterparts.

In another embodiment, the increased concentration of histidine within the plants is achieved by administering a formulation comprising an effective concentration of histidine to the plants. The formulation may be conveniently administered as a foliar spray. The foliar spray would need to contain a relatively high concentration of histidine and be administered at regular intervals. By this method, histidine enters the plants either through the foliage in particular the shoot surfaces, or via the root system, or via both routes.

In another aspect, the invention provides a method of improving the metal accumulating capability of a selected plant, which method comprises transforming plants cells of the selected plant with a recombinant vector comprising a nucleic acid sequence which encodes a polypeptide capable of augmenting the concentration of histidine in the plant cells, the nucleic acid sequence operably linked to an expression control system capable of effecting the expression of the nucleic acid sequence in the plant cells. Successful transformants are selected for and used to produce regenerated transgenic plants.

In further aspects, the invention provides recombinant vectors capable of transforming plant cells in the manner described above, plant cells or plant cell cultures transformed by the vectors, methods of obtaining the vectors and transformed cells, and regenerated transgenic plants having an improved metal accumulating capability compared with their non-transgenic counterparts.

The improved metal accumulating capability achieved according to the invention involves an increase in metal tolerance and/or rate of metal uptake, preferably both. Plants which are not already metal hyperaccumulators may thus be rendered metal hyperaccumulators, although this is not a requirement of the invention. The desired objective is to achieve an increase in the rate of metal extraction out of a unit quantity of soil or other substrate.

The metal can include as well as nickel, cobalt, or zinc, such elements as aluminium, americium, antimony, arsenic, barium, beryllium, bismuth, cadmium, caesium, cerium, chromium, copper, gallium, germanium, gold, indium, iridium, iron, lead, manganese, mercury, molybdenum, neptunium, osmium, palladium, platinum, plutonium, radium, rhenium, rhodium, rubidium, ruthenium, scandium, selenium, silver, strontium, technetium, tellurium, thallium, tin, tungsten, uranium, vanadium, yttrium, including stable or radioactive isotopes of the above. Also included are metalloids, one or more metals in combination, and metals associated with any or various combinations of organic compounds such as oils, fats, grease, fuels, kerosene, phenols, benzene or detergents. The accumulation by plants of any soil contaminants is of interest. In plants having improved metal accumulation properties, elevated metal accumulation may be expected to extend beyond the metal usually bound by the histidine acting as a metal-chelating ligand. It will be a simple matter to test whether a particular modified plant according to the invention is capable of accumulating a significant amount of a particular pollutant in a soil environment.

The plants and plant cells derived from them for use in the invention are preferably chosen from the family Brassicaceae, which is expected to provide the most effective and practical species for this purpose. However, plants from other families are not excluded. Desirable features of plants for use in the invention are favourable growth characteristics for phytoremediation purposes, such as relatively fast growth rates, large and/or deep root systems beneficial for metal extraction from soil, and easy harvesting. Certain members of the genus Brassica are suitable in one or more of these respects.

The amino acid histidine is produced in all plants to some degree and also in microorganisms including bacteria and fungi, but not in mammals (for which it is one of the 10 or so essential amino acids). Thus, recombinant DNA technology can be employed to up-regulate histidine production in a selected plant, e.g. by "over-expressing" one or more of the key genes involved in the histidine biosynthetic pathway. Such over-expression may be achieved by up-regulating the expression of one or more of the plant's own genes; or, more conveniently, it may be achieved by introducing one or more heterologous genes encoding a polypeptide or polypeptides active in the histidine biosynthetic pathway of the selected plant. Suitable heterologous genes may come from known metal hyperaccumulators such as certain species of Alyssum or from bacteria such as *Escherichia coli*. Advantageously, the plant into which they are introduced will have favourable growth characteristics e.g. as discussed above.

Techniques which may be used in the context of the invention for transforming plant cells and regenerating plants from the transformed cells are well-known to those skilled in the art and are reviewed in Gene Transfer to Plants (1995) eds. I Potrykus and G. Spangenberg, Springer-Verlag, Berlin. Transformation may be carried out using an Agrobacterium-based transformation system, with e.g. *A. tumefaciens*, or *A. rhizogenes* which specifically transforms roots. Alternative transformation systems include e.g. biolistic systems.

Techniques and components for construction of vectors according to the invention are also available to those skilled in the art. A vector needs to be chosen which is capable of transforming plant cells, more specifically higher plant cells and the cells of the chosen target or host plant which is to be modified. There will need to be included in the vectors along with the genetic material for increasing histidine production, appropriate expression control sequences which are functional in the selected plant to be transformed. These will usually include a suitable promoter, which may be a constitutively acting or a conditional promoter and could be organ-specific if desired. Preferably an appropriate transcription termination signal will also be present. Another feature which may be included is a signal for directing the polypeptide encoded by the vector to the plastid in a target plant cell, since histidine biosynthesis occurs mainly or exclusively in the plastid. Such a signal may be provided for example by a transit peptide as will be described in more detail later on.

It will be understood that plants having additional modifications concerned with characteristics other than histidine production are not excluded from the invention. In addition to having improved metal accumulation properties, the plants may have modifications, genetic or otherwise, that increase their suitability for phytoremediation.

The invention thus provides a strategy to produce plants with increased effectiveness over conventional varieties in phytoremediation, with an improved ability to accumulate nickel and/or other metals, by virtue of a genetically engineered increase in the amount of histidine within the plant, this property being expressed either constitutively or in response to exposure to metal.

BRIEF DESCRIPTION OF THE DRAWINGS

FIGS. 2(a) and 2(b) are graphs showing changes in amino-acid composition of xylem sap as a response to nickel.

DESCRIPTION OF THE PREFERRED EMBODIMENTS

Figure 1A:
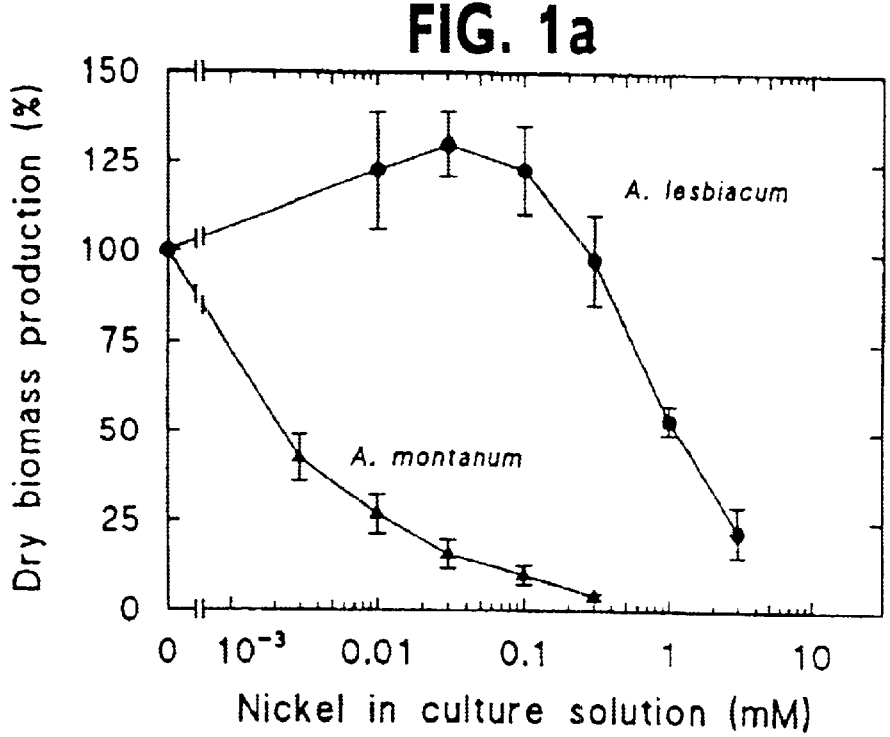
FIGS. 1(a) and 1(b) are graphs showing nickel tolerance and nickel uptake in the hyperaccumulator *Alyssum lesbiacum* (Candargy) Rech.f. and the non-hyperaccumulator *A. montanum* L.

Genetic engineering involving recombinant DNA technologies is now well established as a technique for the manipulation of metabolic pathways in plants (e.g. Hiatt, A., ed. (1993) Transgenic Plants. Marcel Dekker, New York; Trends in Biotechnology, Volume 13, No. 9 (1995); Hughes, M. A. (1996) Plant Molecular Genetics. Longman, Harlow, Essex). This applies also to the enhancement of the production of certain proteinaceous amino acids in free form in plants by genetic modification (reviewed in Lea, P. J. and Forde, B. G. (1994) Plant Cell Environ. 17, 541–556). For example, through the expression of an appropriate gene at high levels (i.e. under the influence of a strong promoter), it has been possible to produce transgenic plants containing elevated concentrations of the amino acids lysine (Shaul, O. and Galili, G. (1992) Plant J. 2, 203–209; Falco, S. C. et al. (1995) Bio/Technology 13, 577–582; Ghislain, M. et al. (1995) Plant J. 8, 733–743; Kwon, T. et al. (1995) J. Plant Physiol. 146, 615–621), threonine (Shaul, O. and Galili, G. (1992) Plant Physiol. 100, 1157–1163), threonine and methionine (Karchi, H. et al. (1993) Plant J. 3, 721–727), and proline (Kavi Kishor, P. B. et al. (1995) Plant Physiol. 108, 1387–1394).

The biosynthetic pathway for histidine has now been completely elucidated in certain microorganisms; in the bacterium *Escherichia coli*, for example, the pathway starting from 5-phosphoribosyl 1-pyrophosphate is known to contain 10 enzyme-catalyzed reactions and to require the products of 8 genes (Alifano, P. et al. (1996) Microbiol. Rev. 60, 44–69; Winkler, M. E. (1996) in *Escherichia coli* and Salmonella: Cellular and Molecular Biology, Second Edition, Vol. I, pp. 485–505. ASM Press, American Society for Microbiology, Washington, D.C.). (Histidine is an "essential" amino acid and cannot be synthesized by mammals: Zubay, G. (1988) Biochemistry, 2nd edition. Macmillan, New York.)

Recent evidence from plants, including the molecular cloning and sequencing of two genes homologous to bacterial genes, suggests that the pathway for histidine biosynthesis in plants is very similar (and perhaps essentially identical) to the pathway in bacteria (Nagai, A. et al. (1991) Proc. Natl Acad. Sci. USA 88, 4133–4137; Tada, S. et al. (1994) Plant Physiol. 105, 579–583; Guyer, D. et al. (1995) Proc. Natl Acad. Sci. USA 92, 4997–5000). The entire pathway of histidine biosynthesis in plants appears to be localized in the plastid (Nagai, A. et al. (1991) loc. cit.; Tada, S. et al. (1994) loc. cit.).

Since the biochemical pathway of histidine biosynthesis is similar and probably highly conserved in bacteria and eukaryotes (Alfani, P. et al. (1996) loc. cit.), it is possible to introduce an appropriate bacterial gene into a plant under the influence of a strong promoter to cause increased rates of histidine production and increased end-product (histidine) accumulation in the genetically modified plant. In the method of choice, the appropriate gene is isolated from the bacterium *Escherichia coli* and introduced to the host plant in the form of a gene construct (as described in detail in the Examples), as it is known that genes from *E. coli* can function successfully in plants to bring about the desired accumulation of metabolic end-products, as for example in the production of transgenic plants that accumulate greatly increased amounts of lysine (transformed *Nicotiana tabacum* plants expressing the *E. coli* dapA gene: Shaul, O. and Galili, G. (1992) Plant J. 2, 203–209), or of mannitol (transformed *Nicotiana tabacum* expressing the *E. coli* mtlD gene: Tarczynski, M. C. et al. (1992) Proc. Natl Acad. Sci. USA 89, 2600–2604).

In the method described, a gene from the pathway of histidine biosynthesis is isolated from *Escherichia coli*, cloned into an appropriate expression vector, transferred using an Agrobacterium-based transformation system into a target or "host" plant such as a variety of Brassica, and used to increase the amount of free histidine in the plant per unit dry biomass.

Particular features of this transformation ("genetic engineering") procedure in the preferred method is the use of a suitable vector containing a cauliflower mosaic virus (CaMV) 35S promoter to give high expression levels for the gene, and use of the transit peptide from a ribulose-1,5-bisphosphate carboxylase-oxygenase (RUBISCO) small subunit polypeptide to aid targeting of the gene product to the plastid (as the entire pathway of histidine biosynthesis occurs in the plastid, as noted above). Experimental methods for this procedure are explained in the Example.

The preferred *E. coli* gene for expression in transformed plants is the hisB gene (GenBank accession number X03416), which is responsible for the conversion of imidazole glycerol phosphate to imidazole acetol phosphate by the enzyme imidazole glycerol phosphate dehydratase (IGPD). (The product of the *E. coli* hisB gene is actually bifunctional [Alfani, P. et al. (1996) loc. cit.], whereas in plants the gene product is monofunctional and catalyzes only the IGPD reaction [Tada, S. et al. (1994) loc. cit.].) The importance of the IGPD reaction is that it is the first step after a branchpoint in the 10-reaction pathway of histidine biosynthesis; whereas the 5 reactions in the latter part of this pathway are unique to the biosynthesis of histidine, the 5 reactions in the former part are shared with a pathway of purine biosynthesis [Alfani, P. et al. (1996) loc. cit. ]. Such branchpoints in metabolic pathways typically have a large controlling influence on flux through that pathway (Zubay G. (1988) loc. cit.; Newsholme, E, A. and Smart, C. (1973 Regulation in Metabolism. Wiley, London), and there is evidence from the effects of specific inhibitors of IGPD (More, I. et al. (1995) Plant Physiol. 107, 719–723) that the IGPD reaction is indeed important in influencing the rate of histidine biosynthesis in plants.

In an alternative method, the product of the *E. coli* hisD gene (EMBL accession number X52656), which encodes the bifunctional enzyme histidinol dehydrogenase catalyzing the last two reactions in the pathway of histidine biosynthesis (Alfani, P. et al, (1996) loc. cit.), is expressed at high levels using an equivalent procedure (also described in the Example). This takes account of the finding that transcript levels for this gene—which has been cloned from a variety of *Brassica oleracea* (Nagai, A. et al. (1991) loc. cit.)—increase significantly in response to blocking of the pathway by a specific inhibition of the IGPD reaction (Guyer et al. (1995) loc. cit.); this may indicate that the product of the hisD gene has an important rate-controlling effect on the production of histidine in plant cells, and consequently is a good target for overexpression of the activity of this enzyme in order to increase the rate of end-product (histidine) synthesis.

In a further alternative method, the product of the *E. coli* hisG gene (GenBank accession number U02070), which encodes the enzyme ATP phosphoribosyltransferase that catalyzes the first reaction in the entire pathway of histidine biosynthesis, is expressed at high levels using an equivalent procedure (also described in the Example). This gene has not so far been cloned from plants. Although as noted above the first part of this pathway is shared with a pathway for purine biosynthesis, the ATP ribosyltransferase enzyme in bacteria is known to be sensitive to feedback inhibition by the end-product of the pathway, histidine. Expression of the hisG gene product in transformed plants can therefore also lead to enhanced production of histidine.

As further alternatives, it is possible to transform the target plant variety using an equivalent procedure with any of the other five genes from *E. coli* that encode enzymes in the pathway of histidine biosynthesis, namely hisI (GenBank accession number ECHISOP, which encodes phosphoribosyl-ATP pyrophosphohydrolase: phosphoribosyl-AMP cyclohydrolase), hisA (GenBank accession number ECHISOP, which encodes phosphoribosyl-formimino 5-amino-1-phosphoribosyl-4-imidazole carboxamide isomerase), hisH (GenBank accession number ECHISOP, which encodes glutamine amidotransferase, a subunit of imidazoleglycerolphosphate synthase), hisF (GenBank accession number ECHISOP, which encodes a cyclase, being the other subunit of imidazoleglycerolphosphate synthase), or hisC (GenBank accession number U02071, which encodes imidazole acetol phosphate aminotransferase) (see Jovanovic, G. et al. (1994) loc. cit.; Alifano, P. et al. (1996) loc. cit.; Winkler, M. E. (1996) loc. cit.). There is, however, no current evidence that these gene products catalyze reactions that greatly influence flux through the metabolic pathway of histidine biosynthesis.

The preferred plants to be used for genetic manipulation and the expression of one or more genes from the bacterium *E. coli* are crop and/or crop-related members of the family Brassicaceae, as defined by Raskin, I. et al. (1994) U.S. Pat. No. 5,364,451 (see also Salt, D. E. et al. (1995) loc. cit.). These cultivars and varieties are established to have favourable growth characteristics for phytoremediation technologies (e.g. high rates of biomass production; large root systems), have favourable harvest characteristics (above-ground parts are readily harvested; plants can produce more than one crop per year; plants will grow in high-density monoculture), and can be genetically modified to express heterologous genes by Agrobacterium-mediated transformation (see Bade, J. B. and Damm, B. (1995) in Gene Transfer to Plants, eds I. Potrykus and G. Spangenberg, pp. 30–38. Springer-Verlag, Berlin; and references cited therein).

Potentially transformed plants are tested for the presence and expression of the heterologous gene(s) by Southern and northern blot hybridization using standard techniques (see Example). They are tested both for enhanced tolerance of one or more metals in growth assays and for enhanced accumulation of one or more metals in the plant biomass under the conditions and using standard techniques such as those described in FIG. 1. Plants with enhanced capacity for metal uptake can be applied for the purposes of decontamination of polluted substrates (phytoremediation) in a variety of situations ranging from soil environments and other substrates with different textures and compositions through to aquatic environments. Plants would be maintained using standard agronomic practices and the metal-containing parts harvested at intervals for processing and safe disposal according to the principles elaborated by Baker, A. J. M. et al. (1995) Mining Environmental Management 3 (September 1995), 12–14; Chaney, R. et al. (1995) ibid. 3 (September 1995), 9–11)

The present invention thus involves a method for producing a greater accumulation of metals in plants than hitherto achieved that will be useful in the phytoremediation of contaminated soils. The invention is based upon our discovery that histidine production is responsible for both the high degree of metal tolerance shown by so-called "metal hyperaccumulator plants" in the genus Alyssum and their characteristic ability to accumulate very high concentrations of metals (in this case up to 2.3% nickel on a dry biomass basis) in their shoots. Circumstantial evidence for this was provided by our earlier (published) discovery that Alyssum plants exposed to nickel showed elevated levels of histidine in their xylem sap. We now have new and surprising evidence that histidine production not only correlates with nickel exposure but is functionally responsible both for nickel detoxification within the plant and for the typical metal-hyperaccumulator phenotype. In other words, this evidence confirms that histidine production within the plant is mechanistically linked both to metal detoxification and to metal hyperaccumulation, and that these are two facets of the same phenomenon.

An important aspect of this finding is that it provides a strategy for producing novel plants with significantly improved capacity for metal uptake from the soil, and hence for the application of such plants in the decontamination of metal-polluted substrates. This strategy may be superior to others based on, for example, enhanced rates of metal uptake into the root system of plants: in the absence of enhanced cellular metal tolerance, such plants will merely be poisoned quickly by the accelerated influx of toxic metal. By contrast, plants showing elevated histidine content, such as those described here, will exhibit both enhanced rates of metal uptake and higher than normal degrees of cellular metal tolerance.

Figure 1B:
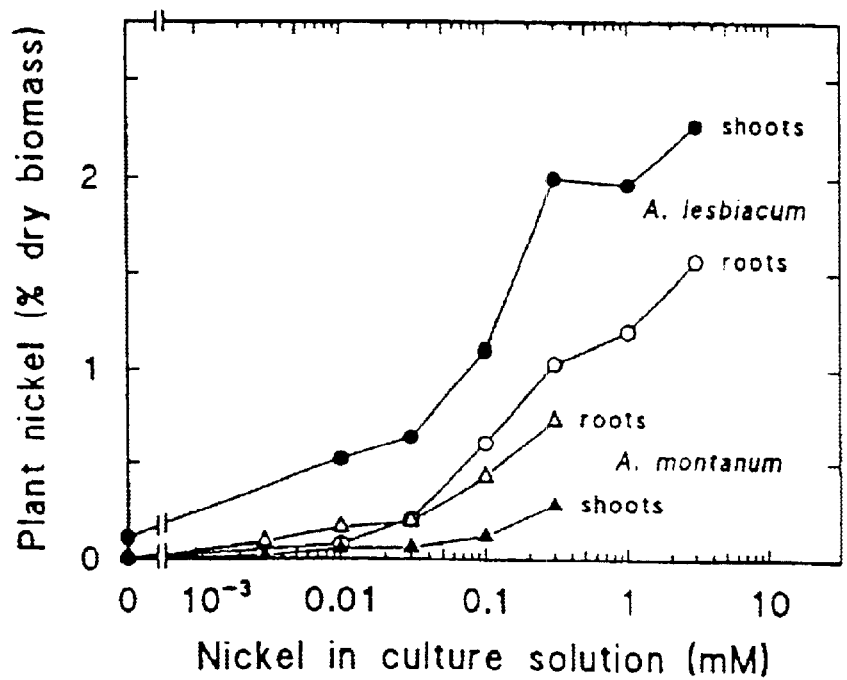

The evidence is as follows.
1. The genus Alyssum (family Brassicaceae) is a large group containing 170 species, of which 48 taxa are known hyperaccumulators of nickel (that are highly nickel-tolerant) and the remainder are non-hyperaccumulators (that are non-tolerant) (Reeves, R. D. (1992) loc. cit.). FIG. 1a shows that under controlled glasshouse conditions with plants raised hydroponically in nutrient-culture solutions the hyperaccumulator *Alyssum lesbiacum* (Candargy) Rech.f. is much more nickel-tolerant than the non-accumulator *A. montanum* L. (the nickel being supplied to the culture solution as nickel sulphate). FIG. 1b shows that the hyperaccumulator *A. lesbiacum* contains elevated concentrations of nickel (up to 2.3% by dry biomass) in its shoots. This implies that the hyperaccumulator species has the ability to translocate nickel very effectively out of the root system into the shoot.
2. Root-pressure exudate was analysed from de-topped root systems to determine the chemical form in which nickel was transported from root to shoot in the xylem. The composition of the xylem sap was similar in both *A. lesbiacum* and *A. montanum*, but in the former there was a very large proportional increase in the concentration of L-histidine in response to exposure of the roots to nickel (FIG. 2a); no other statistically significant change was observed in the concentration of any other xylem amino acid in either *A. lesbiacum* or *A. montanum*. This treatment was also without any statistically significant effect on the concentration of xylem organic-acid anions. These results consequently emphasize the chemical specificity of the elevation in xylem histidine concentration seen in *A. lesbiacum* in response to nickel treatment. Moreover, a direct, linear proportionality was observed between the concentrations of nickel and histidine in the xylem sap (FIG. 2b). A similar response was observed for two other hyperaccumulator species in the genus, *A. murale* and *A. bertolonii* (FIG. 2b), and we infer that this response is characteristic of all hyperaccumulator species in the genus Alyssum. This response is consistent with histidine being synthesized in the roots of the hyperaccumulator species of Alyssum as a specific response to nickel, and thence transported out of the root system in the xylem to the shoot. Histidine is an extremely effective chelator of nickel at physiological pH values: in fact, at the pH values measured in the xylem sap (pH 5.72, mean of 18 samples), as well as at pH values of about pH 7.5 that are typical of cell cytoplasm (Smith, F. A. and Raven, J. A. (1979) Annu. Rev. Plant Physiol. 30, 289–311), histidine shows the highest association constant for complex formation with nickel of any of the naturally occurring organic acids or amino acids (Dawson, R. M. C. et al. (1986) Data for Biochemical Research, 3rd edition. Clarendon Press, Oxford). This accords well with chemical principles, from which a high affinity of nickel for ligands containing nitrogen-donor centres is predicted (Still, E. R. and Williams, R. J. P. (1980) J. Inorg. Biochem. 13, 35–40).
3. Exposing the root system of *A. lesbiacum* to cobalt also elicited a linear increase in xylem histidine concentration, at least over the concentration range below that at which acute cobalt toxicity was apparent (FIG. 2b, inset). Although *A. lesbiacum* is less tolerant to cobalt than to nickel, this species is known to have a significant capacity to hyperaccumulate cobalt (Homer, F. A. (1991) Plant Soil 138, 195–205; Gabbrielli, R. et al. (1991) J. Plant Nutr. 14, 1067–1080). Thus, this result lends further support to the finding of a mechanistic link between histidine production, metal tolerance and metal hyperaccumulation in the genus Alyssum and indicates that the histidine response permits the accumulation within the plant of other metals besides nickel.
4. Similar experiments were conducted with the hyperaccumulator plant *Thlaspi caerulescens* J.&C.Presl (Brassicaceae), which is known to be able to accumulate zinc and nickel as well as other metals (Baker, A. J. M. (1994) loc. cit.). Exposure of these plants in water-culture conditions (as described above) to nickel elicited an increase in histidine concentration in the xylem sap, again (as in *A. lesbiacum*) in direct proportion to nickel. Exposure of the root system to zinc also caused an increase in xylem histidine concentration in proportion to zinc. On a molar concentration basis, less histidine was synthesized in response to zinc than to nickel. Nevertheless, this result establishes that (a) the production of histidine can occur in response to a third type of metal, in this case zinc, and (b) that the production of histidine in response to metal treatment is not limited to members of the genus Alyssum. In consequence, it is reasonable to expect that the phenomenon of metal hyperaccumulation in other genera of plants is also associated with histidine production, and also that the corollary will be true: that production of increased amounts of histidine within the plant will permit the hyperaccumulation of metals by the plant. As a further consequence, the production of increased amounts of histidine within a plant can be expected to allow accumulation to elevated levels of other metals besides nickel, cobalt, or zinc, or of their isotopes including radionuclides, or of metalloids, including such elements as aluminium, americium, antimony, arsenic, barium, beryllium, bismuth, cadmium, caesium, cerium, chromium, copper, gallium, germanium, gold, indium, iridium, iron, lead, manganese, mercury, molybdenum, neptunium, osmium, palladium, platinum, plutonium, radium, rhenium, rhodium, rubidium, ruthenium, scandium, selenium, silver, strontium, technetium, tellurium, thallium, tin, tungsten, uranium, vanadium, yttrium, including one or more metal in combination, and including metals associated with any or various combinations of organic compounds, such as oils, fats, grease, fuels, kerosene, phenols, benzene or detergents.

Figure 3A:
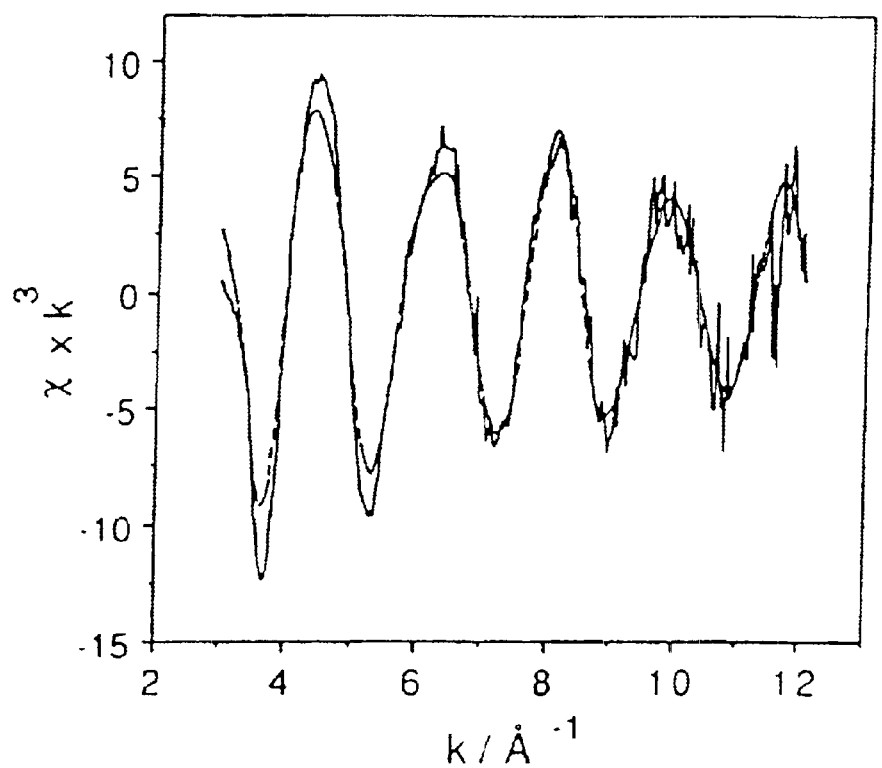
FIGS. 3(a) and 3(b) are graphs showing extended X-ray absorption fine structure (EXAFS) analysis of nickel in xylem sap from *A. lesbiacum*.
Figure 3B:
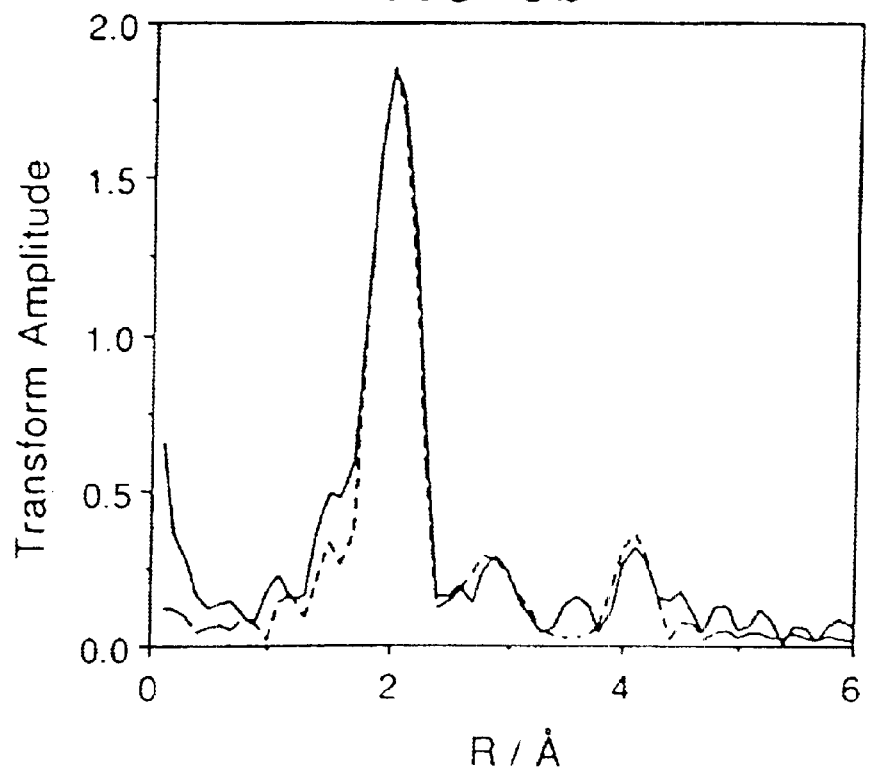

5. Evidence was obtained that the histidine present in the root tissues, xylem sap and shoot tissues of *A. lesbiacum* was effective in chelating nickel using the technique of extended X-ray absorption fine structure (EXAFS) spectroscopy according to the method of J. M. Charnock (1995) Radiat. Phys. Chem. 45, 385–391. The spectrum (FIG. 3a) and corresponding Fourier transform (FIG. 3b) demonstrate that nickel is coordinated with histidine in vivo in these tissues (the continuous line representing the experimental data and the dashed line the best theoretical fit). Significantly, there was no evidence for coordination of nickel by sulphur, for which a bond distance of ca. 2.25 Å would be predicted. This provides a direct demonstration that nickel is chelated predominantly with histidine in the hyperaccumulator *A. lesbiacum,* and not by sulphur-containing ligands such as the metallothioneins and phytochelatins. Consequently, it suggests that the very high degree of cellular tolerance towards nickel in *A. lesbiacum* is attributable to effective metal chelation by histidine. Thus, essentially all the histidine produced in these plants is chelated with the metal ion that induced its synthesis.

Figure 4B:
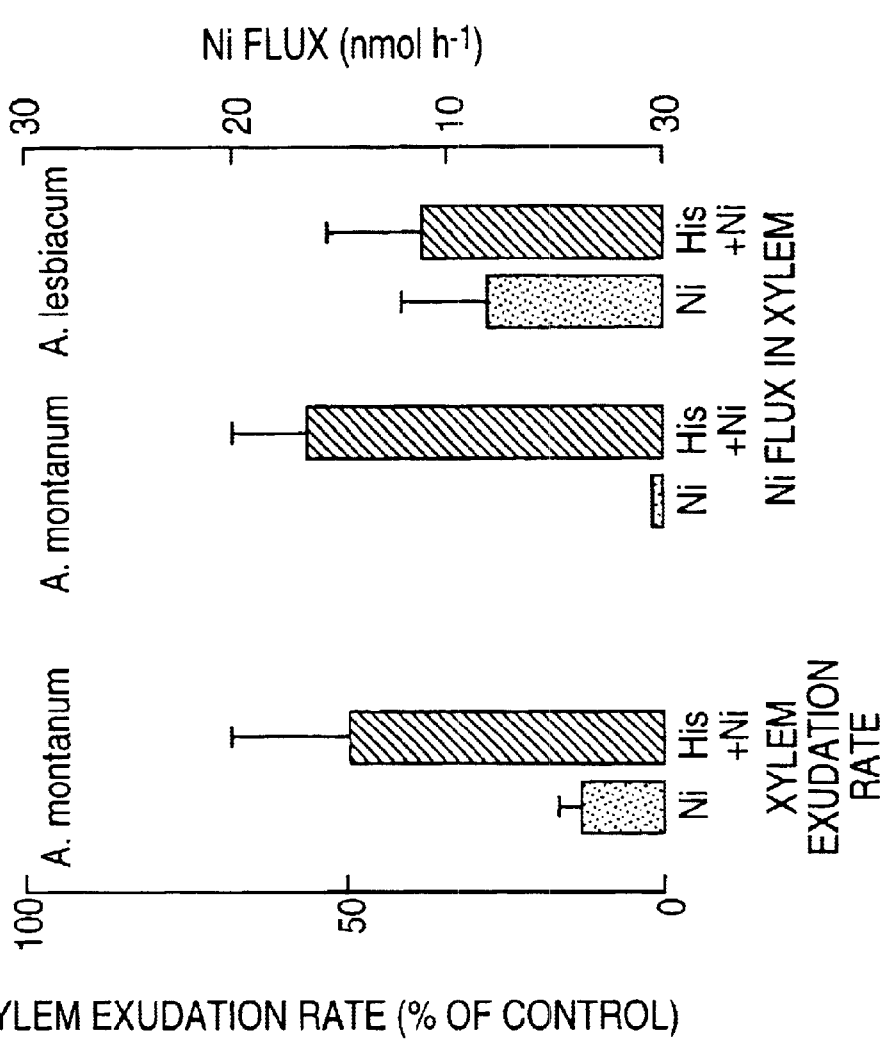
FIGS. 4(a) and 4(b) are graphs showing the effect of exogenously applied histidine on nickel tolerance and xylem nickel translocation.
Figure 4A:
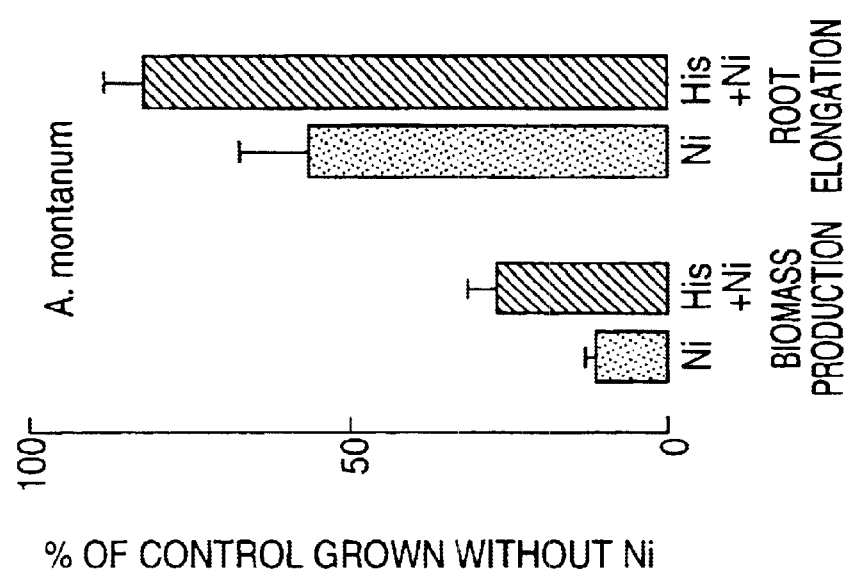

6. To demonstrate that the elevation of histidine levels in the plant were functionally important in nickel detoxification, as opposed to being a correlation without functional significance, the non-accumulator, non-tolerant species *A. montanum* was supplied with high concentrations of histidine (using glutamine as a control) during exposure to nickel in the root medium. At toxic concentrations of nickel in the root medium, 20 mM histidine supplied daily to *A. montanum* as a foliar spray in solution together with the non-ionic detergent Tween 20 (at 0.01%, v/v) considerably reduced the toxic effect of nickel, as evidenced by a more than twofold increase in whole-plant dry biomass production and a halving of the inhibitory effect of nickel on root elongation (FIG. 4a). Furthermore, supplying histidine in the root medium together with nickel moderated the adverse effect of nickel on the rate of xylem-sap exudation, and also greatly increased the flux of nickel through the xylem, as previously noted (FIG. 4b). These results consequently show that histidine is involved in both the mechanism of nickel tolerance and in the effective translocation of nickel from root to shoot that characterizes the typical hyperaccumulator species. That is, the application of relatively high concentrations of histidine exogenously is able to increase markedly both the nickel tolerance of an otherwise non-tolerant species of Alyssum (*A. montanum*) and to cause these plants to translocate nickel out of the root system at much higher rates. Thus, chelation of nickel by histidine is important both in the detoxification of the metal ion within the plant and in facilitating the transport of the metal from root to shoot, a characteristic of metal-hyperaccumulator plants generally (Baker, A. J. M. and Brooks, R. R. (1989) loc. cit.).

Before setting forth the examples, a more detailed description of the Figures is presented hereinbelow.

FIG. 1. Nickel tolerance and nickel uptake in the hyperaccumulator *Alyssum lesbiacum* (Candargy) Rech.f. and the non-hyperaccumulator *A. montanum* L. a, Whole-plant biomass production expressed as percentage of controls grown in the absence of nickel (dry biomass per plant for the controls averaged 27.4±3.1 mg for *A. lesbiacum* and 29.0±4.0 mg for *A. montanum*). Values are means ±SE of four experiments for *A. lesbiacum* and of two experiments for *A. montanum* (n=10 plants per treatment). b, Nickel concentrations in dry biomass of roots and shoots. Values are means of two independent experiments, in each of which material was pooled from 10 plants.

METHODS. Plants were germinated for 7 d on floating nets in 1 mM $Ca(NO_3)_2$ solution, subsequently transferred to 1.2–1 culture vessels (10 plants per vessel), and supplied with modified 0.1-strength Hoagland solution containing 0.1 mM $KH_2PO_4$, 0.5 mM $KNO_3$, 0.4 mM $Ca(NO_3)_2$, 0.2 mM $MgSO_4$, 0.01 mM FeNaEDTA, 0.01 mM $H_3BO_3$, 2 $\mu$M $MnSO_4$, 0.2 $\mu$M $ZnSO_4$, 0.2 $\mu$M $CuSO_4$, 0.1 $\mu$M $Na_2MoO_4$ and 0.02 mM NaCl, supplemented with 0, 0.01, 0.03, 0.1, 0.3, 1, or 3 mM $NiSO_4$. Plants were grown in a glasshouse at night temperatures between 14° C. and 18° C. and day temperatures between 22° C. and 34° C. with supplementary lighting provided by sodium-vapour lamps to give a 16-h photoperiod. Culture solutions were continuously aerated and exchanged every 7 d; solution pH remained in the range 5.6 to 6.0. Plants were harvested after 18 d, rinsed with distilled water, dried at 80° C. for 48 h and weighed. For analysis, duplicate samples of dried plant material were ashed in a muffle furnace (16 h at 400° C., followed by 24 h at 500° C.), dissolved in 20% (w/v) HCl, and nickel quantified in diluted solutions containing 1% (v/v) $H_2SO_4$ and 0.04% (w/v) $LaCl_3$ using a Perkin Elmer 3030 atomic absorption spectrophotometer.

FIG. 2. Changes in amino-acid composition of xylem sap as a response to nickel. a, Ratios of xylem amino-acid concentrations in plants exposed to nickel in the root medium (0.3 mM $NiSO_4$ for *A. lesbiacum,* 0.003 mM for *A. montanum*) relative to amino-acid concentrations in the xylem sap of control plants (0 mM $NiSO_4$). Ratios were calculated from the means of values from four independent batches of plants, within each of which five plants were pooled for analysis. Amino acids are listed from left to right in order of decreasing abundance in the xylem sap of *A. lesbiacum* controls; only those amino acids present at 0.002 mM in any sample are shown. The dotted line indicates a ratio of 1. The only significant change observed in xylem amino-acid concentrations for either species was for histidine in *A. lesbiacum* (P<0.001; two-sided t-test of primary data for controls versus nickel-treated plants). The principal xylem organic-acid anions determined by HPLC using a Bio-Rad HPX-87H ion-exclusion column were citrate and malate, but neither changed significantly in either species on exposure to nickel (citrate and malate concentrations, assayed according to Bergemeyer, H. U., ed. (1985) Methods of Enzymatic Analysis, 3rd edition, Vol. VII. VCH, Weinheim, averaging 0.30 mM and 0.15 mM, respectively, in *A. lesbiacum,* and 0.20 mM and 0.05 mM, respectively, in *A. montanum*). b, Relationship between nickel and histidine concentrations in xylem sap of *A. lesbiacum* and two other hyperaccumulator species (*A. murale* Waldst. & Kit. and *A. bertolonii* Desv.). Regression analysis yielded the equation y=0.186 x+0.072 ($r^2$=0.851, d.f.=63, P<0.001). The inset shows the equivalent relationship between xylem cobalt and histidine concentrations for *A. lesbiacum,* fitted by the equation y=0.376 x+0.003 ($r^2$=0.945, d.f.=10, P<0.001). Data were obtained through analysis of root-pressure exudates obtained as xylem sap from de-topped root systems of plants grown at a range of nickel or cobalt concentrations (0 to 3 mM NiSO$_4$, or 0 to 0.03 mM COSO$_4$, added to the nutrient solution described in FIG. 1).

METHODS. Plants were cultivated after germination (7 d) for 4 weeks as in FIG. 1 and were then transferred to nickel-containing solutions for 8 d prior to sampling. To obtain xylem sap, shoots were excised 0.5 h after the onset of the dark period, the cut surfaces of the hypocotyls blotted with absorbent tissue, and root-pressure exudate collected over 8 h. Samples were analyzed for inorganic cations by atomic absorption spectrophotometry. Amino acids were analyzed using an Applied Biosystems PTC C-18 reverse-phase column (220×2.1 mm) in an ABI 420A derivatizer/analyzer after pre-column derivatization with phenylisothiocyanate; amino acids were separated at 34° C. by applying a sodium acetate/acetonitrile gradient in water.

FIG. 3. Extended X-ray absorption fine structure (EXAFS) analysis of nickel in xylem sap from *A. lesbiacum*. a, Normalized oscillatory EXAFS amplitude, weighted by $k^3$, plotted against the photoelectron wave vector (k). b, Associated Fourier transform (R is the distance of scattering atoms from the primary absorber). Continuous lines are experimental data and broken lines the best theoretical fit.

METHODS. Xylem sap, collected after exposing plants to 0.3 mM Ni in the root medium for 8 d as described in FIG. 2, was injected into a perspex sample cell with Mylar windows and frozen in liquid nitrogen. EXAFS data were collected at 77 K in fluorescence mode at the nickel K-edge using a Canberra 13-element solid-state detector on station 8.1 at the Daresbury Synchrotron Radiation Source, operating at 2 GeV with an average current of 150 mA. Eight scans were averaged and the spectra analyzed, including multiple scattering, using the Daresbury program EXCURV92; theoretical fits were generated by adding shells of scatterers around the central nickel atom and iterating bond lengths and Debye-Waller type factors to obtain the best fit to the experimental data (Charnock, J. M. (1995) Radiat. Phys. Chem. 45, 385–391).

FIG. 4. Effect of exogenously applied histidine on nickel tolerance and xylem nickel translocation. a, Effect of foliar spraying with histidine (compared with glutamine) on nickel tolerance of *A. montanum*, assayed as the effect on whole-plant dry biomass production and root elongation. After germination for 7 d, plants were grown in modified Hoagland solution (FIG. 1) containing either 0 or 0.03 mM NiSO$_4$ for 23 d and were sprayed daily with a solution of either 20 mM glutamine (Ni) or 20 mM histidine (His+Ni), both containing 0.01% (v/v) of the non-ionic detergent Tween 20. Values of biomass production and root elongation are for nickel-treated plants expressed as percentages of the respective controls grown in the absence of nickel. Each bar represents the mean of 9 plants+1 SE. Biomass production (P<0.001) and root elongation (P=0.010, both one-sided t-tests) were significantly greater in nickel-treated plants sprayed with histidine compared with glutamine. b, Effect of histidine supplied in the root medium on xylem-sap exudation rate and on nickel flux in *A. montanum* and *A. lesbiacum* exposed to 0.3 mM NiSO$_4$. Roots of 4-week-old plants were excised and exposed to a root medium of modified Hoagland solution supplemented with either 0.3 mM MgSO$_4$ (controls) or 0.3 mM NiSO$_4$, with or without 0.3 mM added histidine. Xylem exudate was collected over 12 h. Each bar represents the geometric mean of 10 samples+1 SE. For *A. montanum*, both xylem exudation rate and nickel flux were significantly greater at P<0.001 in the presence of histidine (ANOVA); no significant differences were observed in *A. lesbiacum* (exudation rates not shown).

The foregoing examples are presented to demonstrate certain embodiments of the present invention. Other embodiments not described are also possible. Therefore, the spirit and scope of the appended claims should not be limited to the foregoing examples.

EXAMPLES

Example 1

A. Gene Isolation

Unless otherwise stated, DNA manipulations in the following are carried out according to the standard procedures described in Sambrook, J. et al. (1989) Molecular Cloning: A Laboratory Manual, 2nd Edition. Cold Spring Harbor Laboratory Press, Cold Spring Harbor, N.Y.

Genes encoding enzymes in the pathway of histidine biosynthesis are isolated from *Escherichia coli* K-12. Cells of *E. coli* are grown on LB medium according to Sambrook, J. et al. (1989) loc. cit. To isolate genomic DNA, bacterial cultures grown to saturation (cell density=3 optical density units) are centrifuged for 3 min at 13,000 g. The bacterial pellet is resuspended in 700 μl of lysis buffer (20 mM Tris-HCl [pH 8.0], 10 mM NaEDTA, 10 mM DTT, 0.5% [v/v] SDS) and 5.5 μl of freshly prepared Proteinase K (20 mg ml$^{-1}$ stock) is added. The samples are incubated at 37° C. for 1 h. Each sample is then subjected to three phenol:chloroform:isoamyl alcohol (24:24:1 [v/v]) extractions, followed by three further extractions using water-saturated chloroform, to remove protein; at each stage the organic phase is discarded. After the final extraction, the aqueous layer is mixed with 0.1 volume of 3 M sodium acetate (pH 5.0) and an equal volume of isopropanol and stored at -20° C. for 30 min. The precipitated DNA is pelleted by centrifugation at 13,000 g at 4° C. for 10 min. The DNA pellets are washed twice with 70% (v/v) ethanol and air-dried briefly. The pellets are resuspended in 25 μl of 25 mM Tris-HCl (pH 7.5) and 0.5 mM NaEDTA.

Genes encoding the required enzymes from the pathway of histidine biosynthesis in *E. coli* are isolated and cloned from the genomic DNA prepared as above using the polymerase chain reaction (PCR) (Innis, M. A. et al., eds (1990) PCR Protocols: A Guide to Methods and Applications. Academic Press, Inc., San Diego). Primers for the PCR are designed according to the general principles of optimal primer design described in Innis, M. A. et al. (loc. cit.). Specifically, in the preferred method using the hisB gene from *E. coli* (Carlomagno, M. S. et al. (1988) J. Mol. Biol. 203, 585–606; Alifano, P. et al. (1996) loc. cit.; GenBank accession number X03416), which encodes the bifunctional gene product imidazoleglycerolphosphate dehydratase (EC 4.2.1.19) and histidinolphosphate phosphatase (EC 3.1.3.15), the primer 5'-ACGC<u>GCATGCA</u>-TGAGTCAGAAGTATCTTTTTATCGA-3' (SEQ ID NO: 1) is designed to the 5' end of the gene (and incorporating the SphI restriction site as shown underlined), and the primer 5'-ACGC<u>GTCGAC</u>TTACAGCACCCTTTCGACGAGG-3' (SEQ ID NO: 2) is designed to the 3' end of the gene (incorporating the SalI restriction site as shown underlined).

Similarly, in an alternative method, the hisD gene (Carlomagno, M. S. et al. (1988) loc. cit.; Jovanovic, G. et al. (1994) J. Mol. Biol. 239, 433–435; Alifano, P. et al. (1996) loc. cit.; EMBL accession number X52656), which encodes the bifunctional gene product histidinol dehydrogenase (EC 1.1.1.23), is isolated and cloned using the PCR primers 5'-ACGC<u>GCATGC</u>ATGAGCTTTAACAC-AATCATTGACTG-3' (SEQ ID NO: 3) and 5'-ACGC <u>GTCGAC</u>TCATGCTTGCTCCTTAAGGGCG-3' (SEQ ID NO: 4) (incorporating the SphI and SalI restriction sites, respectively, as denoted by the underlined nucleotides).

Similarly, in a further alternative method, the hisG gene (Carlomagno, M. S. et al. (1988) loc. cit.; Jovanovic, G. et al. (1994) J. Mol. Biol. 239, 433–435; Alifano, P. et al. (1996) loc. cit.; GenBank accession number U02070), which encodes the gene product ATP phosphoribosyltransferase (EC 2.4.2.17), is isolated and cloned using the PCR primers 5'-ACGC<u>GCATGC</u>ATGACAGACAACACT-CGTTT ACGC- 3' (SEQ ID NO: 5) and 5'-ACGC<u>GTCGAC</u>TCACTCCATCATCTTCTCAATCGG-3' (SEQ ID NO: 6) (incorporating the SphI and SalI restriction-enzyme sites, respectively, as denoted by the underlined nucleotides).

In further alternative methods, PCR primers may be designed using similar principles to isolate and clone any of the other five genes from *E. coli* that encode enzymes in the pathway of histidine biosynthesis, namely hisI (GenBank accession number ECHISOP, which encodes phosphoribosyl-ATP pyrophosphohydrolase: phosphoribosyl-AMP cyclohydrolase; EC 3.5.4.19), hisA (GenBank accession number ECHISOP, which encodes phosphoribosyl-formimino-5-amino-1-phosphoribosyl-4-imidazole carboxamide isomerase; EC 5.3.1.16), hisH (GenBank accession number ECHISOP, which encodes glutamine amidotransferase, a subunit of imidazoleglycer-olphosphate synthase), hisF (GenBank accession number ECHISOP, which encodes a cyclase, being the other subunit of imidazoleglycerolphosphate synthase), or hisC (GenBank accession number U02071, encodes imidazole acetol phosphate aminotransferase [otherwise known as histidinol phosphate aminotransferase]; EC 2.6.1.9) (see Jovanovic, G. et al. (1994) loc. cit.; Alifano, P. et al. (1996) loc. cit.; Winkler, M. E. (1996) loc. cit.).

PCR is conducted using 1.2 $\mu$g ml$^{-1}$ of *E. coli* genomic DNA with 50 pmol of each of the two synthesized oligonucleotide primers appropriate to the gene to be isolated in a reaction volume of 100 $\mu$l containing 200 $\mu$M dNTPs, 10 mM Tris-HCl (pH 8.3), 50 mM KCl, 2 mM MgCl$_2$ and 0.5 units of *Thermus aquaticus* DNA polymerase. Template and primers are initially denatured at 96° C. for 3 min followed by an amplification process consisting of a temperature-step cycle of 96° C. for 30 s (denaturation), 65° C. for 30 s (annealing) and 68° C. for 60 s (extension), this cycle being repeated 35 times; the reaction is completed with a final incubation for 60 s at 65° C. (annealing) followed by extension for 5 min at 68° C. The entire PCR product is electrophoresed according to Sambrook et al. (1989) loc. cit. and cDNA isolated from the gel using GeneClean (BIO101, Inc) according to the manufacturer's instructions. The PCR product is restricted for 12 h with SphI at 37° C., followed by a digestion for 7 h with SalI at 37° C. The DNA is extracted into the aqueous phase against phenol:chloroform:isoamyl alcohol (24:24:1 [v/v]) and chloroform:isoamyl alcohol (24:1 [v/v]) once each. The DNA is then ethanol-precipitated and resuspended in a final volume of 11 $\mu$l to give a concentration of 145 ng DNA $\mu$l$^{-1}$. The PCR product (1.5 $\mu$g) is then ligated with 100 ng $\mu$l$^{-1}$ of SphI- and SalI-restricted pGEM-5ZF vector cDNA (Promega) using T4 ligase enzyme for 12 h at 16° C. The ligated cDNA is then used to transform XL-1 Blue *E. coli* cells (Stratagene). To obtain plasmid DNA to check for the presence of the cDNA insert, minipreps are performed using a Wizard Miniprep kit (Promega) on transformants containing the newly created plasmid. The presence of the cDNA insert is confirmed by restriction digest analysis with SphI and SalI and by DNA sequencing.

B. Vector Construction

For expression of the appropriate *E. coli* gene in a plant, a suitable construct is made containing the required *E. coli* cDNA insert together with the necessary transcription and translation elements. For example, the *E. coli* hisB gene is subcloned into the SphI/SalI site in the expression cassette of pJIT117 (Guerineau, F. et al. (1988) Nucleic Acids Res. 16, 11380), which contains the cauliflower mosaic virus (CaMV) 35S promoter with a duplicated enhancer for strong constitutive expression, the transit peptide of the small subunit of ribulose-1,5-bisphosphate carboxylase-oxygenase (RUBISCO) to target the fusion protein into the plastid stroma, and the CaMV poly(A) tail. (In the event that the short N-terminal extension from the RUBISCO small subunit inhibits the enzymatic activity of the HisB protein, other vectors not containing the N-terminal codons of the mature RUBISCO small subunit polypeptide [described by Guerineau, F. (1995) in Plant Gene Transfer and Expression Protocols, ed. H. Jones. Humana PreRs Inc., Totowa, N.J., pp. 1–32] may be used for vector construction.)

To integrate the expression cassette containing the appropriate *E. coli* gene (e.g. hisB) into the plant genome, the cassette is first cloned into a binary vector system which is used for transforming plant cells. In the present example, the expression cassette is cloned into the KpnI site of the disarmed binary vector pBinI9 (Bevan, M. (1984) Nucleic Acids Res. 12, 8711–8721). This plasmid contains part of the nptIII gene conferring kanamycin resistance as a selectable marker.

C. Plasmid Transfer

The binary vector pBinI9 containing the required expression cassette is propagated in *E. coli*, the plasmid DNA isolated, and cells of an appropriate *Agrobacterum tumefaciens* strain such as MOG301 (Bade, J. B. and Damm, B. (1995) loc. cit.) transformed with this DNA by electroporation using standard techniques (Shaw, C. H. (1995) in H. Jones, ed., loc. cit., pp. 32–37).

D. Plant Transformation

In the present example, *Agrobacterium tumefaciens* strain MOG301 containing the required plasmid is prepared for plant transformation by culturing overnight in liquid LB medium containing antibiotics and subcultured as described by Bade, J. B. and Damm, B. (1995) loc. cit. In the preferred method, *Brassica oleracea* is used for transformation (De Block, M. et al. (1989) Plant Physiol. 91, 694–701). Hypocotyl segments are cut from the plants, washed, and pre-incubated with callus-inducing medium; the explants are then incubated with log phase *Agrobacterum tumefaciens* containing the plasmid for 20 to 60 minutes; co-cultivated after removal of the bacterial suspension; transferred after washing to shoot-inducing medium in petri dishes; transferred when regenerating shoots are apparent to shoot-longation medium; and finally transferred to root-inducing medium, and thereafter when roots have formed to soil, all these steps being performed according to the protocol and conditions described by Bade, J. B. and Damm, B. (1995) loc. cit. and De Block, M. et al. (1989) loc. cit.

E. Analysis of Transformed Plant Lines

Potentially transformed plants of, in this example, *Brassica oleracea* are characterized for the expression of the appropriate *E. coli* gene by Southern and northern hybridization analysis using the cognate cDNA as a probe to establish whether the individual plants are true transformants. Those lines expressing the corresponding transcript at high levels are tested for enhanced tolerance towards nickel and for enhanced nickel accumulation using the experimental methods described in FIG. 1. These plants are also tested using equivalent procedures for tolerance towards other metals and for their ability to accumulate these other metals. Further tests of these plants growing in soil are used to evaluate the potential of these individual lines for the extraction of metals from soils under conditions equivalent to those at known field sites suffering from metal contamination.

What is claimed is:

1. A method for removing metal from a metal-containing substrate, which comprises:

providing a transgenic plant of the Brassicacea family which is genetically transformed to express a heterologous nucleic acid sequence encoding a histidine biosynthesis enzyme, and growing the transgenic plant on the metal-containing substrate under conditions suitable for the transgenic plant to accumulate and remove metal from the substrate, wherein the transgenic plant produces an increased amount of histidine in comparison to a corresponding nontransgenic plant, and wherein the transgenic plant accumulates and removes an increased amount of metal in comparison to a corresponding nontransgenic plant.

2. The method according to claim 1, wherein the nucleic acid sequence encoding the histidine biosynthesis enzyme is obtained from *E. coli*.

3. A recombinant vector, comprising a heterologous nucleic acid sequence encoding a histidine biosynthesis enzyme, operably linked to an expression control system which expresses the nucleic acid sequence in a plant of the Brassicacea family.

4. A transgenic plant cell of the Brassicacea family, which is transformed with the recombinant vector according to claim 3, wherein the transgenic plant cell produces an increased amount of histidine in comparison to a corresponding nontransgenic plant cell, and wherein the transgenic plant cell accumulates and removes an increased amount of metal in comparison to a corresponding nontransgenic plant cell.

5. A transgenic plant cell culture of the Brassicacea family, which is transformed with the recombinant vector according to claim 3, wherein the transgenic plant cell culture produces an increased amount of histidine in comparison to a corresponding nontransgenic plant cell culture, and wherein the transgenic plant cell culture accumulates and removes an increased amount of metal in comparison to a corresponding nontransgenic plant cell culture.

6. A regenerated transgenic plan of the Brassicacea family, which is transformed with the recombinant vector according to claim 3, wherein the regenerated transgenic plant produces an increased amount of histidine in comparison to a corresponding regenerated nontransgenic plant, and wherein the regenerated transgenic plant accumulates and removes an increased amount of metal in comparison to a corresponding regenerated nontransgenic plant.

7. A method of improving the metal uptake capability of a plant of the Brassicacea family, which comprises transforming cells of a plant of the Brassicacea family with the recombinant vector according to claim selecting a tranformed plant cell having an improved metal uptake capability in comparison to a corresponding nontransformed plant cell, and regenerating a transgenic plant from the selected transformed plant cell, wherein the regenerated transgenic plant has an improved metal uptake capability in comparison to a corresponding regenerated nontransformed plant.

8. A method of obtaining a transgenic plant cell for regeneration to a transgenic plant having improved metal accumulating capability in comparison to a corresponding nontransgenic plant, which comprises transforming cells of a plant of the Brassicacea family with the recombinant vector according to claim 3, and selecting a tranformed plant cell having an improved metal uptake capability in comparison to a corresponding nontransformed plant cell, whereby the transformed plant cell is suitable for regeneration to a transgenic plant having an improved metal uptake capability in comparison to a corresponding nontransgenic plant.

\* \* \* \* \*